United States Patent [19]

Vora et al.

[11] Patent Number: 5,012,021

[45] Date of Patent: Apr. 30, 1991

[54] PROCESS FOR THE PRODUCTION OF ALKYLAROMATIC HYDROCARBONS USING SOLID CATALYSTS

[75] Inventors: Bipin V. Vora, Darien; Paul R. Cottrell, Arlington Heights, both of Ill.

[73] Assignee: UOP, Des Plaines, Ill.

[21] Appl. No.: 584,214

[22] Filed: Sep. 18, 1990

Related U.S. Application Data

[63] Continuation-in-part of Ser. No. 290,479, Dec. 29, 1988, abandoned.

[51] Int. Cl.$^5$ .............................................. C07C 2/66
[52] U.S. Cl. .................................... 585/315; 585/323; 585/455; 585/456
[58] Field of Search ................. 585/315, 323, 455, 456

[56] References Cited

U.S. PATENT DOCUMENTS 4,523,048 6/1985 Vorz ..................................... 585/323

Primary Examiner—Curtis R. Davis

Attorney, Agent, or Firm—Thomas K. McBride; John G. Tolomei

[57] ABSTRACT

An improved process for the production of alkylaromatic hydrocarbons is disclosed. Paraffinic hydrocarbons are dehydrogenated to yield an olefin-containing stream, which is later charged to an alkylation zone for reaction with an aromatic hydrocarbon in the presence of a solid alkylation catalyst. The olefin-containing stream is first passed through a selective hydrogenation zone in which diolefins are converted to monoolefins by contact with a selective catalyst. This increases the yield and the quality of the product alkylate by greatly reducing the production of biphenyl compounds and oligomers in the alkylation zone. Process efficiency is improved by passing unconverted paraffinic and monoolefinic hydrocarbons from the alkylation zone through another hydrogenation zone for the saturation of monoolefinic hydrocarbons and recycling the saturated stream to the dehydrogenation zone. The use of a solid alkylation catalyst can also allow the selective hydrogenation zone to be located downstream of the stripper for the dehydrogenation zone so that the effluent from the selective hydrogenation zone discharges directly into the alkylation zone.

7 Claims, 1 Drawing Sheet

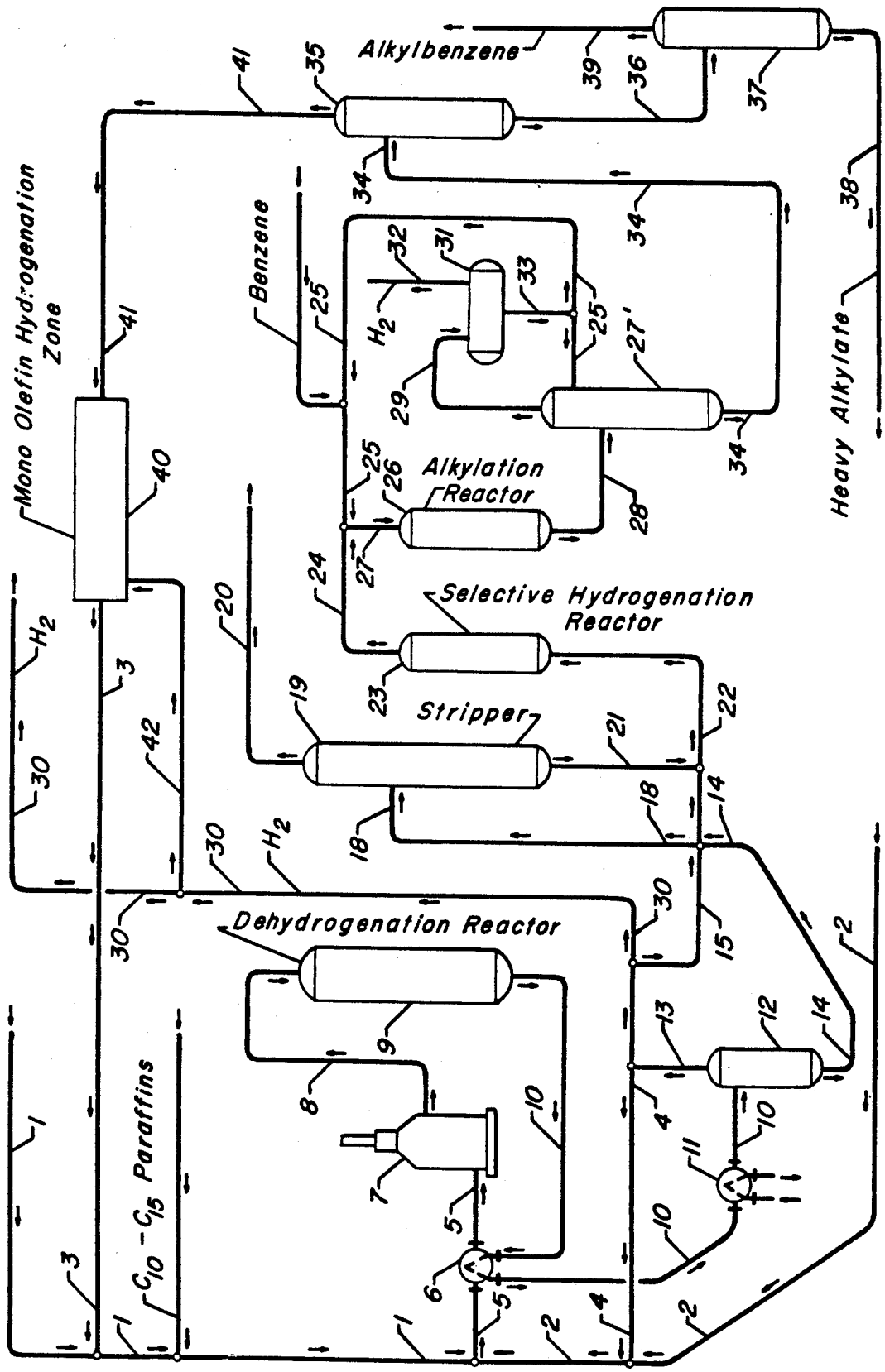

PROCESS FOR THE PRODUCTION OF ALKYLAROMATIC HYDROCARBONS USING SOLID CATALYSTS

FIELD OF THE INVENTION

1. Cross-Reference to Related Applications

This application is a continuation-in-part of pending application Ser. No. 290,479, filed Dec. 29, 1988, and now abandoned, the contents of which are incorporated herein by reference.

The invention relates to the broad field of hydrocarbon processing. The invention may also be broadly classified as relating to a process for the production of alkylaromatic hydrocarbons. More specifically, the invention relates to an integrated hydrocarbon conversion process in which dehydrogenation, selective hydrogenation, and alkylation reactions are performed. The invention is directly concerned with a reduction in by-product formation and an improvement in alkylate product in the alkylation zone that uses a solid bed catalyst.

2. Information Disclosure

The production of alkylaromatic hydrocarbons by the combined steps of paraffin dehydrogenation and aromatic alkylation using the resultant olefinic hydrocarbons is an established commercial process. In the past, hydrogen fluoride (HF) was a preferred alkylation catalyst. There are a variety of flow schemes for using an integrated HF alkylation zone as illustrated in U.S. Pat. No. 3,484,498 issued to R. C. Berg and U.S. Pat. No. 3,494,971 issued to E. R. Fenske. The former reference illustrates the passage of a normal paraffin charge stream into a dehydrogenation zone, with the effluent of this zone passing through a condenser (not shown) in which the vapor phase reactor effluent is partially condensed. The resultant mixed phase material is passed into a separating zone in which it is separated into a hydrogen-rich recycle stream and a liquid phase process stream. The liquid phase process stream is passed through a stripping zone which preferably comprises a trayed fractionation column. Hydrocarbons which remain after stripping of the light hydrocarbons are passed into an alkylation zone in admixture with benzene or other aromatic hydrocarbons. The effluent of the alkylation zone is passed into a fractionation system which produces several effluent stream including a product stream and a normal paraffin recycle stream which is directed into the dehydrogenation zone. The Fenske reference also illustrates the combination of a dehydrogenation zone with an alkylation zone, but supplies further details as to a preferred arrangement of the alkylation zone. These references also describe functional dehydrogenation catalysts and conditions.

U.S. Pat. No. 3,696,160 issued to K. D. Chomyn is pertinent for its teaching that those skilled in the art of hydrocarbon processing are aware that it may be beneficial to selectively hydrogenate diolefins to monoolefins in certain hydrocarbon streams. This reference is directed to the selective conversion of propadiene and butadiene contaminants in propylene and butene charge stocks employed in alkylation processes for the production of aviation and motor fuel. In the alkylation process, a $C_3$–$C_4$ feed stream is converted to a high octane $C_7$–$C_8$ product. It is stated that a small diolefin content in the alkylation feed stream is undesirable because of increased acid consumption as a result of forming tarry acid-diolefin condensation products, which decreases the profitability of the process. The reference indicates that supported nickel and palladium catalysts are excellent hydrogenation catalysts in the diolefin conversion service, but that their tendency to deactivate in sulfur-containing feedstocks limits their utilization. The reference discloses the use of a sulfided nickel-tungsten catalyst.

U.S. Pat. No. 3,655,621 issued to A. S. Kasperik et at. illustrates a process for the selective hydrogenation of $C_4$ diolefins in an alkylation feed stream employing a catalyst comprising presulfided nickel supported on a refractory base. In U.S. Pat. No. 3,234,298 issued to W. C. van Zijll Langhout et al., a process is disclosed for the selective hydrogenation of light, diene-containing cracked hydrocarbon oils. This process is employed to increase the stability of such materials as pyrolysis gasoline and kerosene obtained by severe thermal cracking operations. Such hydrogenation is desirable to reduce the gum-forming characteristics and other undesirable properties of these hydrocarbon mixtures. The process is described as being applicable to diene-containing hydrocarbons ranging from $C_3$–$C_{18}$ in carbon number. The process employs a catalyst comprising sulfided nickel on alumina or sulfided molybdenum on alumina.

U.S. Pat. No. 3,472,763 issued to J. Cosyns et al. is pertinent for its description of a selective diolefin hydrogenation catalyst which comprises nickel supported on an alumina substrate having a number of specified characteristics and for its teaching of the utility of this catalyst. Specifically, it is taught that this catalyst may be employed for the conversion of all types of conjugated diolefins to monoolefins and in particular to the conversion of aliphatic conjugated diolefins having up to 15 carbon atoms per molecule to the corresponding monoolefins. The invention is also described as being useful in the selective hydrogenation of alpha alkenyl aromatic hydrocarbons to the corresponding alkylaromatic hydrocarbons. Another application of the process is the selective hydrogenation of gasolines containing diolefins and other gum-forming hydrocarbons.

The use of catalysts which comprise palladium supported on a refractory material is described in U.S. Pat. No. 3,662,015 issued to Y. Komatsu et al.; U.S. Pat. No. 4,409,401 issued to T. P. Murtha; and U.S. Pat. No. 4,409,410 issued to J. Cosyns et al.

U.S. Pat. No. 4,523,048 issued to B. Vora teaches an integrated process for producing alkylaromatic hydrocarbons that uses selective hydrogenation to remove diolefins from a dehydrogenation zone effluent by use of a selective hydrogenation zone located between a hydrogen separator and a light ends stripper. The process arrangement of the Vora reference is specifically suited for the use of HF alkylation catalyst.

It is well known that aromatic compounds can be alkylated with olefins over solid-oxide type catalysts, a wide variety of specific compositions for solid bed catalysts are disclosed in the art. U.S. Pat. No. 3,201,487 issued to S. Kovach et al. discloses a catalyst comprising chromia on a silica-alumina base for the alkylation of aromatic hydrocarbons. U.S. Pat. No. 4,358,628 issued to L. Slaugh describes the use of tungsten oxide on a silica-alumina base to provide a support catalyst for the alkylation of aromatics with detergent range olefins. The alkylation of aromatic hydrocarbons with monoolefins using boria and a Group IVA or Group VIIB metals on alumina support is disclosed by S. Kovach in U.S. Pat. No. 4,489,213. A stabilized perfluorinated polymersulfonic acid for the alkylation of arenes and alkenes is discloses in U.S. Pat. No. 4,673,679 issued to D. Farcasiu. A number of zeolitic catalysts, suitable for use as solid alkylation catalysts, are disclosed in U.S. Pat. No. 3,751,506; 4,387,259; and 4,409,412.

BRIEF SUMMARY OF THE INVENTION

The invention provides an improved process for the production of alkylaromatic hydrocarbons by using a solid alkylation catalyst. This process eliminates or at least substantially reduces the concentration, in the alkylation zone effluent stream, of undesirable by-products including biphenyl compounds, indanes, and tetralins. Besides increasing the purity of the desired monoalkylated benzenes, the subject process also increases the yield of these desired compounds. These improved results are obtained through the use of a selective hydrogenation reactor placed at a unique location between the dehydrogenation and alkylation zone and a monoolefin hydrogenation zone for the saturation of a recycle stream from the alkylation zone. This arrangement requires only a very minimal increase in the complexity and capital costs of the process to achieve a greatly significant improvement in operational performance.

In one embodiment, this invention is a multistep process for the production of alkylaromatic hydrocarbons and the recycle of unconverted hydrocarbons from an alkylation zone. The process includes combining a $C_6$–$C_{22}$ paraffinic hydrocarbon feed and a saturated recycle stream and passing the combined stream through a dehydrogenation reaction zone maintained at dehydrogenation conditions to produce a vapor phase dehydrogenation reactor effluent stream comprising $C_6$-minus light hydrocarbons, hydrogen and $C_6$–$C_{22}$ paraffinic, monoolefinic and diolefinic hydrocarbons. After cooling and at least partial condensing a dehydrogenation effluent stream is passed to a vapor liquid separation zone and separated into a vapor stream comprising hydrogen and a liquid phase stream comprising dissolved hydrogen, $C_6$-minus light hydrocarbons, and $C_6$–$C_{22}$ diolefinic, paraffinic and monoolefinic hydrocarbons. The liquid phase stream is passed with a controlled amount of hydrogen to a selective hydrogenation reaction zone containing a selective hydrogenation catalyst and maintained at selective hydrogenation conditions. In the selective hydrogenation zone, essentially all of the diolefins are converted to monoolefins to produce a selective hydrogenation reaction zone effluent substantially free of $C_6$–$C_{22}$ diolefinic hydrocarbons. The selective hydrogenation zone effluent stream and an aromatic hydrocarbon enter an alkylation zone maintained at alkylation promoting conditions and containing a solid alkylation zone catalyst to alkylate the aromatic hydrocarbon and produce an alkylation zone effluent comprising an alkylaromatic hydrocarbon and $C_6$–$C_{22}$ paraffinic and monoolefinic hydrocarbons. Alkylaromatic hydrocarbon products are separated from the effluent and the $C_6$–$C_{22}$ paraffins and monoolefins are passed with hydrogen to a monoolefinic hydrocarbon hydrogenation zone. Contact with a hydrogenation catalyst at hydrogenation conditions converts essentially all of the monoolefinic hydrocarbons to paraffinic hydrocarbons and produces the saturated recycle stream that enters the dehydrogenation reaction zone.

A highly preferred embodiment of this invention may accordingly be characterized as a multistep process for the production of alkylbenzenes. The process comprises the steps of passing a paraffin feed stream which comprises at least one $C_{10}$-plus linear paraffinic hydrocarbon through a dehydrogenation reaction zone and forming a vapor phase dehydrogenation reaction zone effluent stream which comprises a mixture of hydrogen, mono- and diolefinic $C_{10}$-plus linear hydrocarbons, and $C_{10}$-plus linear paraffins. After separating hydrogen from the dehydrogenation reaction zone effluent stream by partially condensing the dehydrogenation reaction zone effluent stream and separating the resultant two-phase admixture in a vapor-liquid separating zone, a vapor phase stream, which is rich in hydrogen, is withdrawn and a liquid phase process stream comprising $C_{10}$-plus linear paraffins, dissolved hydrogen, and mono- and diolefinic $C_{10}$-plus linear hydrocarbons is passed through a selective hydrogenation zone maintained at diolefin selective hydrogenation conditions and in which the liquid process stream is contacted with a solid selective hydrogenation catalyst to form a selective hydrogenation zone effluent stream which contains less than 0.4 mole percent $C_{10}$-plus diolefinic hydrocarbons. The effluent stream from the selective hydrogenation zone enters an alkylation zone maintained at alkylation-promoting conditions where it is contacted with a solid alkylation catalyst to produce an alkylation zone effluent stream which comprises $C_{10}$-plus linear paraffins and monoolefins and alkylbenzenes. The alkylbenzenes are recovered from the alkylation zone effluent as a product stream and the $C_{10}$-plus linear paraffins and monoolefins are recovered as a recycle stream. Passage of the recycle stream through an additional hydrogenation zone converts the monoolefins to linear paraffins. The recycle stream now containing essentially all paraffins is returned to the dehydrogenation reactor as part of the previously described $C_{10}$-plus linear paraffinic hydrocarbons.

BRIEF DESCRIPTION OF THE DRAWING

The drawing is a simplified process flow diagram of a dehydrogenation and alkylation process arranged in accordance with a preferred embodiment of the invention.

DETAILED DESCRIPTION OF THE INVENTION

The production of alkylaromatic hydrocarbons by the sequential steps of paraffin dehydrogenation followed by an alkylation reaction is a well established commercial process. The product alkylaromatic hydrocarbons are tailored to a specific need through the choice of the feed paraffinic hydrocarbon and feed aromatic hydrocarbon. An example of this integrated process which has achieved widespread commercial success is the production of linear alkylbenzenes suitable for use in the production of detergent. These alkylated benzenes are often referred to in the art as detergent alkylate and the process is referred to as a detergent alkylation process. It is known to those skilled in the art that these processes currently generate a small but significant amount of undesired by-product hydrocarbons, which normally have a higher molecular weight and higher boiling point than the desired alkylebenzene. These undesired by-products are normally separated from the linear alkylbenzenes in the product recovery zone and concentrated into a stream referred to generically as heavy alkylate.

It is an objective of the subject invention to reduce the amount of heavy alkylate which is produced in an integrated detergent alkylation process. It is a further objective of the subject invention to improve the quality of the detergent alkylate produced in such an integrated process by reducing the production of undesired by-products which fall within the boiling point range of the desired alkylaromatic hydrocarbons.

There are two feed hydrocarbons consumed in the subject process. These feed hydrocarbons are a paraffinic hydrocarbon and an aromatic hydrocarbon. The paraffinic hydrocarbon is preferably a straight chain (unbranched) or normal paraffinic hydrocarbon having from 6 to 22 carbon atoms per molecule. A better quality detergent precursor normally results from the use of olefinic hydrocarbons having from about 10 to 15 carbon atoms per molecule. It is, therefore, preferred that the feed paraffinic hydrocarbon is a $C_{10}$ to $C_{15}$ paraffin. The feed paraffinic hydrocarbon is normally charged to the process as a mixture of paraffins having different carbon numbers. A preferred method for the production of the paraffinic hydrocarbons is the extraction of straight chain hydrocarbons from a hydrotreated kerosene boiling range petroleum fraction. In other applications of the subject process, it may be preferred to charge a branched paraffinic hydrocarbon. These branched chain paraffins can be obtained by extraction or by suitable oligomerization and treatment processes. The aromatic hydrocarbon which is alkylated in the subject process is preferably benzene, but a higher molecular weight aromatic hydrocarbon may also be charged to the process. The feed aromatic hydrocarbon may, therefore, be toluene, a xylene, ethylbenzene, phenol, naphthalene, etc.

In the subject process, the feed paraffinic hydrocarbons are first converted to olefinic hydrocarbons in a dehydrogenation zone. The unseparated paraffin/olefin mixture produced as the effluent of the dehydrogenation zone is then passed into the alkylation zone as the olefin-containing feed stream. This is basically because of the high cost of separating olefins and paraffins of the same carbon number, but the presence of the paraffins can also be beneficial as by decreasing the overall olefin concentration in the alkylation reactor and acting as a heat sink for the heat of reaction. The olefin-containing feed stream charged to the alkylation zone may, therefore, contain from about 30 to about 92 mole percent straight chain paraffins having the same number of carbon atoms per molecule as the olefinic hydrocarbon. These relatively non-reactive paraffins pass through the alkylation zone in various hydrocarbon phase streams and are eventually separated from the alkylate by fractionation and then recycled to the dehydrogenation zone.

It has now been found that the objective set forth above can be achieved through modification of the process between the dehydrogenation section and alkylation section of the integrated process. This modification comprises the location of a reactor for the selective hydrogenation reactor. This selective hydrogenation converts at least a substantial amount of the diolefinic hydrocarbons to monoolefinic hydrocarbons, which are the desired product of the dehydrogenation section. At the same time, the concentration of undesired diolefinic hydrocarbons in the net effluent of the dehydrogenation section of the process is decreased. The lower concentration of diolefinic hydrocarbons in the alkylation zone results in a reduced production of by-product including oligomers and biphenyl hydrocarbons. It has been found that equipment required to perform the selective hydrogenation can be minimized by performing the hydrogenation step just upstream of the alkylation zone. This provides a low cost and facile method of performing the hydrogenation.

For purposes of discussion, the subject integrated process may be divided into a dehydrogenation section and an alkylation section. The dehydrogenation section will preferably be configured substantially in the manner shown in the drawing. In this arrangement, a fresh paraffinic hydrocarbon feed stream is combined with recycle hydrogen and recycled unconverted hydrocarbons from the alkylation section. This forms a reactant stream which is heated and passed through a bed of a suitable catalyst maintained at the proper dehydrogenation conditions of temperature, pressure, etc. The effluent of this catalyst bed or reactor effluent stream is usually cooled and partially condensed. Part of the uncondensed material is employed as a hydrogen-rich recycle gas stream. The remainder of the uncondensed hydrogen-rich material is the net production of hydrogen which may be used elsewhere in the process or in other applications such as desulfurization. As used herein, the term "rich" is intended to indicate a molar concentration of the indicated compound or class of compounds above 50%. The separation zone also normally produces a liquid stream referred to herein as the liquid phase process stream. This stream is basically an admixture of dehydrogenated and undehydrogenated acyclic hydrocarbons. This liquid phase stream will also contain some dissolved hydrogen and light hydrocarbons produced by various cracking reactions which occur at the high temperatures employed in the dehydrogenation reactor.

The composition of the dehydrogenation catalyst is not believed to materially affect the operation of the subject process provided this catalyst meets commercial standards for activity, stability, and selectivity. Dehydrogenation catalysts are described in U.S. Pat. Nos. 3,274,287; 3,315,007; 3,315,008; 3,745,112; and 4,430,517. These catalysts are comprised of a platinum group component supported on a porous carrier material. The preferred carrier material is a refractory inorganic oxide such as gamma-alumina. The preferred dehydrogenation catalysts contain on an elemental basis 0.01 to 2 wt. % platinum group component and about 0.1 to 5 wt. % of an alkali or alkaline earth metal. Preferably, there is present 0.05 to 1 wt. % platinum group component and about 0.25 to 3.5 wt. % of the alkali or alkali or alkaline earth component. The platinum group component may be chosen from the group consisting of platinum, palladium, rhodium, ruthenium, osmium, and iridium, but platinum is highly preferred. The alkali or alkaline earth component may be selected from the group consisting of the alkali metals—cesium, rubidium, potassium, sodium, and lithium; and the alkaline earth metals—calcium, strontium, barium, and magnesium. This component is preferably either lithium or potassium, with lithium being especially preferred. Another example of a suitable dehydrogenation catalyst is a catalyst which in addition to the previously described platinum and alkali or alkaline earth metal components contains a tin component. This catalytic composite would contain from about 0.1 to about 1 wt. % tin. Yet another catalytic composite which should be highly suited for use in the subject process comprises an indium component in addition to the platinum, tin, and alkali or alkaline earth components. The indium component may be present on an elemental basis equal to about 0.1 to about 1 wt. % of the final composite. It is also known in the art that some catalytic composites of this nature may benefit from the presence of a small amount of a halogen component, with chlorine being the normally preferred halogen. Typical halogen concentrations in the final catalytic composite range from about 0.1 to about 1.5 wt. %. A halogen component is not desired in all situations. These catalytic composites are known to those skilled in the art and are described in the available references.

This effluent of the separation zone is either passed into a stripping column or directly into a selective hydrogenation zone. The stripping column is designed and operated to remove all compounds which are more volatile than the lightest normal hydrocarbon which it is desired to charge to the alkylation section of the integrated process. These light materials will be concentrated into a net overhead stream which will comprise an admixture of hydrogen and light hydrocarbons. The purpose of the stripping operation is to eliminate the light hydrocarbons from the recycle stream which returns paraffinic hydrocarbons to the dehydrogenation zone. The passage of light monoolefins into the alkylation zone would also lead to the production of an increased amount of undesired side products through alkylation and polymerization reactions. If the effluent of the separation zone is passed directly to a selective hydrogenation zone, the effluent of the selective hydrogenation zone is usually passed into a stripping section of the type previously described.

In the subject process, a liquid phase process stream is withdrawn from this separation zone and passed into a selective hydrogenation reaction zone. This zone contains a selective hydrogenation catalyst and is maintained at conditions necessary for selective hydrogenation of diolefins to monoolefins. The placement of the selective hydrogenation zone downstream of the separation zone makes it very simple and, therefore, very economical to perform the desired selective hydrogenation. One reason for this is that the reactants are in the desired liquid phase state as they leave the separation zone. A second reason is that the temperature of the liquid phase process stream as it leaves the separation zone will normally be within the desired operating range of the selective hydrogenation reaction zone.

The use of a solid catalyst in the alkylation zone may also make it possible to locate the selective hydrogenation reaction zone downstream of the stripping section since the small amounts of hydrogen that enter the alkylation zone with the selective hydrogenation zone effluent will not interfere with the process. Such an arrangement was not possible when HF acid catalyst was employed in the alkylation zone, since it would be necessary to vent this hydrogen from the alkylation zone and it would, therefore, be necessary to treat the vented hydrogen stream for the removal of vapor phase HF. Thus, an additional advantage to this process flow is that it may allow the effluent from the selective hydrogenation reactor to flow into the alkylation zone without intermediate separation.

The selective hydrogenation conditions employed in the hydrogenation zone are preferably similar to that maintained in the stripping zone of the prior art processes. More specifically, the minimum pressure should be sufficient to maintain the reactants as liquid phase hydrocarbons. A broad range of suitable operating pressures, therefore, extends from about 270 to about 7000 kPag, with a pressure between about 340 and 2070 kPag psig being preferred. A relatively moderate temperature between about 40° and 400° C. is preferred. More preferably, the hydrogenation zone is maintained at a temperature between about 100° and about 300° C. The liquid hourly space velocity of the reactants through the selective hydrogenation zone should be above 1.0. Preferably, it is above 5.0 and more preferably it is between 5.0 and 35 $hr^{-1}$. The optimum set of conditions will, of course, vary depending on such factors as the composition of the feed stream and the activity and stability of the hydrogenation catalyst.

Another operating condition which may vary depending on catalyst is the ratio of hydrogen to diolefinic hydrocarbons maintained within the selective hydrogenation zone. Some catalysts, such as a palladium on alumina catalyst which was tested, require a higher hydrogen concentration to achieve the desired degree of hydrogenation. Therefore, with some catalysts such as the palladium catalysts, it may be desired to operate with a hydrogen to diolefinic hydrocarbon mole ratio of between 2:1 and 5:1. With the catalyst, it was determined that hydrogen concentrations above this range resulted in the saturation of a significant amount of monoolefinic hydrocarbons. This, of course, is undesirable as it reduces the yield of the process. With the preferred nickel sulfide catalyst, there should be less than 2.0 times the stoichiometric amount of hydrogen required for the selective hydrogenation of the diolefinic hydrocarbons, which are present in the liquid phase process stream, to monoolefinic hydrocarbons. Preferably, the mole ratio of hydrogen to diolefinic hydrocarbons in the material entering the selective hydrogenation zone is maintained between 1:1 and 1.8:1.

The selective hydrogenation zone preferably comprises a single fixed bed reactor containing a cylindrical bed of catalyst through which the reactants move in a vertical direction. It is preferred that the reactants flow upward through the reactor as this provides good mixing. The catalyst may be present as pellets, spheres, extrudates, irregular shaped granules, etc. The prior art suggests the use of a number of metals on the selective hydrogenation catalyst including tungsten, palladium, silver, molybdenum, and nickel. Of these catalysts, it is preferred that the active catalytic metal component present in the hydrogenation catalyst is either nickel or palladium, with nickel being especially preferred. When non-noble metals are employed, the catalyst should have a high concentration or loading of the active metal, with the metal component preferably comprising over 2 wt. % of the catalytic composite. More preferably, over 5 wt. % of the catalytic composite is metallic. It is very highly preferred that the selective hydrogenation catalyst also includes a sulfur component. The preferred catalyst may, therefore, be described as a sulfided nickel catalyst. The preparation of catalysts of this nature is described in U.S. Pat. No. 3,919,341. The preferred selective hydrogenation catalyst has a lower sulfur concentration than the catalyst described in this reference, with sulfur levels between about 0.1 and 0.4 wt. % being preferred. The basic function of the sulfur component is believed to be the attenuation of the hydrogenation activity of the nickel. It is known in the art that carbon monoxide may be passed into a selective hydrogenation reactor for the purpose of moderating or attenuating the hydrogenation reaction. The use of carbon monoxide and other such moderators though not necessary may be employed.

The selective hydrogenation catalyst also comprises a support or carrier material which should be relatively inert and refractory to the conditions employed within the process. The support can be formed from a variety of porous materials including various clays, diatomaceous earth, aluminas, ceramics, attapulgus clay, and other synthetically prepared or naturally occurring silicates, kaolin, kieselguhr, titania, alumina, crystalline aluminosilicates, and admixtures of two or more of these materials. The especially preferred carrier material is an alumina. Of the aluminas, gamma-alumina is preferred. The carrier material or support may have an apparent bulk density of about 0.3 to about 0.8 g/cc, a surface area of about 50 to about 550 $m^2/g$, and a pore volume of between about 0.1 and about 1.0 ml/g.

The effluent of the dehydrogenation section, after passing through the selective hydrogenation section, is passed to an alkylation section which comprises an alkylation zone and a fractionation or recovery section. The alkylation zone can have a number of different configurations and will use a solid alkylation catalyst. The use of a particular solid alkylation catalyst is not essential to this invention. Such solid catalysts typically are characterized as having an acid function and are, therefore, better known as solid acid catalysts. Such solid acid catalysts include, but are not limited to, materials such as amorphous silica-alumina, crystalline aluminosilicate materials also known as zeolites, naturally occurring and man-made clays including pillared clays, acidic polymer catalysts and any other solid catalysts that are known to be acidic in nature.

Amorphous silica-alumina materials would comprise one group of materials useful as a solid acid catalyst in the alkylation reaction zone. The useful amorphous silica-alumina may be utilized alone or it may be modified with known catalytic modifiers or it may be modified by methods known in the art to tailor physical properties such as catalyst pore volume distribution, catalyst strength, etc. Examples of such catalyst may be found in U.S. Pat. Nos. 4,358,628, and 3,084,204.

Another solid acid catalyst useful in the alkylation of an aromatic substrate with an olefin acting agent are catalysts that comprise crystalline aluminosilicate materials also commonly known as zeolites. Any zeolite which contains acidic sites may be useful as a solid alkylation catalyst. Such zeolites may be modified with catalytic modifiers or modified to increase or attenuate the acidity of the particular zeolite. Examples of and/or zeolite containing catalysts that are useful solid alkylation catalysts are disclosed in U.S. Pat. Nos. 4,570,027, and 4,547,065.

Additionally, a solid acid catalyst can consist of an acidic polymer either impregnated upon a solid support or shaped into a catalyst particle. Such materials comprising, for example, fluorinated sulfonic acid components in the polymer matrix have been known to be useful in aromatic alkylation reactors. One particularly useful acidic polymeric catalyst is described in U.S. Pat. No. 4,661,441. Other examples of acidic polymeric catalysts useful in the alkylation of an aromatic hydrocarbon are found in U.S. Pat. Nos. 4,547,474, 4,056,578, 4,683,216 and the like.

It should be noted that the types of solid catalysts mentioned above only comprise a small portion of the types of solid catalysts that may be useful in a solid bed catalyzed aromatic alkylation process. Other catalysts known to have acidic properties and not mentioned are likely to be able to function as aromatic alkylation catalysts and, therefore, fall within the scope of catalysts useful in the solid bed alkylation step of this invention.

Conditions within the alkylation zone are selected to promote the alkylation reaction and will depend on the type of solid alkylation used in the alkylation zone as well as the particular aromatic and olefinic reactants. Suitable operating conditions for the alkylation zone will usually include a liquid hourly space velocity of from 0.01 to 5 and temperatures in the range of 40° C. to 300° C. with temperatures of 100° C. to 200° C. being particularly preferred. Pressures in the alkylation are most often selected to maintain liquid phase conditions and include a pressure in the range of 600 to 3450 kPag.

The solid bed alkylation reaction zone will usually consist of a fixed bed down flow type reactor. One of the by-products of the reaction is the formation of gum-type polymers that tend to accumulate on the surface of the catalyst and block reaction sites. Therefore, the reaction zone typically includes means for regenerating the catalyst by removing the gum-type polymers from its surface. A variety of solvents are known that can remove these polymers from the surface of the catalyst. A preferred reactor arrangement consists of two parallel reactors that alternately receive feed and a hot benzene wash so that one reactor is making product while the other undergoes regeneration. In addition to benzene washing, the regeneration technique may include a carbon burning step for certain catalysts such as inorganic acids, zeolite or alumina-silica.

The alkylation zone effluent enters separation facilities for the recovery of products and recyclable starting materials. Suitable fractionation facilities for such separations are well known by those skilled in the art and can be tailored as desired to provide specific fractions and purities. A typical separation section that would find use in the highly preferred embodiment of this invention includes a benzene column, a paraffin column, and a rerun column. The benzene column is operated under conditions effective to cause the division of the entering hydrocarbons into a high purity benzene stream which is removed as the overhead liquid and a bottoms stream containing paraffins and the alkylate product. This bottoms stream is passed into the paraffin column. The non-reactive paraffins along with unreacted monoolefins are removed as an overhead liquid stream and recycled to the dehydrogenation zone. The bottoms stream of the paraffin column comprises the product alkylate and any higher molecular weight by-product hydrocarbons formed in the reaction zone. The paraffin column bottoms stream is passed into a rerun column which produces a high purity overhead stream containing a detergent alkylate. A bottoms stream comprising polymerized olefins and polyalkylated benzenes (heavy alkylate) is fractionated from the rerun column as heavy by-product. The paraffin and the rerun columns are normally operated at a subatmospheric pressure.

Regardless of the specific method, the separation facilities will ordinarily include some method for recycling linear paraffins to the dehydrogenation zone. Through solid alkylation catalyst, initially may convert 100% of olefins, with time some deactivation occurs which will leave some unconverted olefins that enter the paraffin recycle. Therefore, the alkylation zone effluent entering the separation section may contain some monoolefins. Although it would be desirable to directly recycle these monoolefins back to the alkylation zone, the aforementioned difficulty of separating the monoolefins from the non-reactive linear paraffins of same carbon number precludes such an arrangement. As a result, the paraffins separated from the alkylation zone effluent may ordinarily contain from 0.1 to 2.0 wt. % olefins.

Olefins in the feed to the dehydrogenation reaction zone are highly undesirable since they increase coke make in the reaction zone and shorten the life of currently available dehydrogenation catalyst. Therefore, in this invention, the recycle stream is passed through a hydrogenation zone, referred to as a monoolefin hydrogenation zone, to convert olefins in the recycle stream to their corresponding paraffins. Unlike the previously described selective hydrogenation zone, the monoolefin hydrogenation zone is designed to fully saturate all the hydrocarbons charged thereto while minimizing any cracking or polymerization of hydrocarbons passing therethrough. As a result, the monoolefinic hydrogenation may take on many forms, but preferably comprises a fixed bed reaction zone in which all of the entering materials are contacted with a hydrogenation catalyst at hydrogenation conditions. Because of the relatively small concentration of monoolefins, the monoolefinic hydrogenation zone may comprise a small guard-bed type reactor. A broad range of hydrogenation conditions includes an LHSV (liquid hourly space velocity based at 15° C. liquid) between about 2° to 500° C. A preferred range of hydrogenation conditions include an LHSV of 10 to 70, a pressure of 70 to 700 kPag, and a temperature of 50° to 300° C. Hydrogen is passed through the hydrogenation zone on a once-through basis and excess hydrogen becomes a part of the feed to the dehydrogenation zone. As described previously, the dehydrogenation zone employs noble metal catalyst and requires $H_2$ recycle to suppress coking, therefore, additional hydrogen may also be introduced to the dehydrogenation zone.

A broad range of catalysts are commercially available for the hydrogenating zone. Suitable catalyst for this process will completely saturate mono- and any trace polyolefinic hydrocarbons without significant cracking or polymerization activity. Such catalysts will normally comprise one or more metallic components which may be an elemental metal or a metal compound. The metals are normally chosen for Groups VIII and IVA of the Periodic Table of the elements. Pd, Pt and Ni are preferred metals for these catalysts. The metallic components of the catalyst are supported by a refractory inorganic oxide material such as one of the aluminas, silica, silica-alumina mixtures, various clays and natural or synthetic zeolitic materials, Preferably, the carrier material is alumina. Metallic components may be added to the carrier which is in the form of spheres, pellets or extrudates by impregnation, cogelation or coprecipitation. Preferably, the metallic components are impregnated by immersing an extruded particle in an aqueous solution of a metal containing compound and thereafter treating the impregnated particle by drying, calcination or other treatments.

A complete operation of the process can be more fully understood from a process flow for a preferred embodiment.

Referring now to the drawing, a paraffin feed stream comprising an admixture of $C_{10}$–$C_{15}$ normal paraffins is charged to line 1. The normal paraffins are combined with a stream of recycle paraffins from line 3. The paraffins are admixed with hydrogen from line 2 and other normal paraffins from line 3 and passed through line 5.

A mixture of paraffins and hydrogen flowing through line 5 is first heated in the indirect heat exchanger 6 and is then passed into a fired heater 7. The resultant vapor phase mixture of paraffins and hydrogen is passed through line 8 into a dehydrogenation reactor 9. Inside the reactor 9, the paraffins are contacted in the presence of a dehydrogenation catalyst at conditions which effect the conversion of a significant amount of the paraffins to the corresponding olefins. There is thus produced a reactor effluent stream carried by line 10 which comprises a mixture of hydrogen, unconverted paraffins, $C_{10}$–$C_{15}$ monoolefins, and a smaller amount of $C_{10}$–$C_{15}$ diolefins and $C_1$–$C_9$ hydrocarbons produced as undesired by-products of the dehydrogenation reaction. This reactor effluent stream is first cooled by indirect heat exchange in the heat exchanger 6 and is then further cooled in the indirect heat exchange means 11. This cooling is sufficient to condense substantially of the $C_{10}$-plus hydrocarbons into a liquid phase process stream and separate the liquid phase stream from the remaining vapor, which is rich in hydrogen. This mixed phase stream enters the vapor-liquid separation vessel 12 wherein it is divided into a hydrogen-rich vapor phase stream removed through line 13 and a liquid phase process stream removed through line 14. The vapor phase stream is divided into a net hydrogen product stream removed through line 30 and a hydrogen recycle stream carried by line 4, a make-up hydrogen stream carried by line 15 to a selective hydrogenation zone 23, and a make-up hydrogen stream carried by line 42 to a hydrogenation zone 40.

The liquid phase process stream removed from the bottom of the separator 12 contains unconverted $C_{10}$–$C_{15}$ paraffins, $C_{10}$–$C_{15}$ mono- and diolefins, lighter hydrocarbons produced as reaction by-products, and some dissolved hydrogen. The liquid phase portion effluent of the separator is then passed through line 18 to a stripper column 19. In this column, the light hydrocarbons produced in the dehydrogenation reactor as by-products and any remaining unconsumed hydrogen are separated from the $C_{10}$-plus hydrocarbons and concentrated into a net overhead stream removed from the process through line 20.

The remainder of the hydrocarbons entering the stripper are concentrated into a net bottoms stream carried by line 21. A controlled volume of hydrogen from line 15 is admixed into the liquid process stream. It is then passed through line 22 into a selective hydrogenation reactor 23. In this reactor, the liquid phase hydrocarbons and hydrogen are contacted with a catalyst under conditions which promote the selective hydrogenation of diolefins to monoolefins.

The effluent from the selective hydrogenation reactor is transferred via a line 24. This stream comprises an admixture of $C_{10}$–$C_{15}$ paraffins and monoolefins and has a greatly reduced concentration of diolefins compared to the dehydrogenation reactor effluent. This admixture is combined with benzene from line 25 and passed into an alkylation reactor 26 through line 27. In the alkylation zone, the benzene and olefinic hydrocarbons are admixed in the presence of an alkylation catalyst at alkylation-promoting conditions.

The alkylation zone effluent stream carried by a line 28 and passed into a benzene fractionation column 27' by a line 28. This stream comprises an admixture of unreacted benzene, $C_{10}$–$C_{15}$ paraffins, and the product alkylbenzenes. These compounds are separated in column 27' into a bottoms stream and an overhead stream comprising hydrogen, trace amounts of light hydrocarbons, and benzene. The overhead stream is carried by line 29 to a separator drum 31 from which hydrogen and light gases are removed via a line 32 and condensed liquid is withdrawn by a line 33 to supply reflux to column 26 and benzene for recycle to line 25. A line 34 carries the remainder of the alkylation zone effluent from column 27' to a paraffin column 35 from which a bottoms stream comprising alkylbenzene products and heavy alkylate by-products is taken by a line 36. The contents of line 36 are separated by a rerun column 37 into a bottoms stream 38 comprising heavy alkylate and an overhead stream 39 comprising alkylbenzenes.

Overhead from paraffin column 35 is a recycle stream the comprises a mixture of linear paraffins and monoolefins that are transferred to a monoolefin hydrogenation zone 40 by a line 41. Hydrogenation zone 40 receives a controlled amount of hydrogen from line 30 via a line 42. Passage of the recycle stream through hydrogenation zone completely saturates unconverted olefins and provides a recycle of linear paraffins that are transferred to the reaction zone via line 3.

The FIGURE shows a preferred arrangement for the integrated dehydrogenation-alkylation scheme of this invention. This description is not meant to preclude other arrangements for the process flow of this invention. For instance, a useful modification of the process passes the entering paraffin through the monoolefin hydrogenation zone to saturate olefins in the incoming feed. Another useful variation combines the separate selective hydrogenation reactor and alkylation reactor into a single reaction vessel containing separate beds of hydrogenation and alkylation catalysts.

What is claimed is:

1. In a process for the production of an alkylaromatic hydrocarbon by the reaction of an aromatic hydrocarbon with monoolefinic hydrocarbons in the presence of paraffinic hydrocarbons wherein a $C_6$–$C_{22}$ paraffinic hydrocarbon feed and a recycle stream are combined and the combined stream is passed through a dehydrogenation reaction zone maintained at dehydrogenation conditions effective to produce a vapor phase dehydrogenation reactor effluent stream comprising $C_6$-minus light hydrocarbons, $C_6$–$C_{22}$ paraffinic hydrocarbons, $C_6$–$C_{22}$ monoolefinic hydrocarbons, $C_6$–$C_{22}$ diolefinic hydrocarbons and hydrogen, that is cooled and partially condensed to form a vapor-liquid dehydrogenation reactor zone effluent that is passed to a vapor-liquid separation zone to separate said vapor-liquid dehydrogenation reactor effluent stream into a vapor phase process stream comprising hydrogen and a liquid phase process stream comprising dissolved hydrogen, $C_6$-minus light hydrocarbons, $C_6$–$C_{22}$ diolefinic hydrocarbons, $C_6$–$C_{22}$ paraffinic hydrocarbons and $C_6$–$C_{22}$ monoolefinic hydrocarbons which is passed with a hydrogen feedstream through a selective hydrogenation reaction zone containing a selective hydrogenation catalyst that is maintained at selective hydrogenation conditions, wherein said amount of hydrogen in said hydrogen feedstream is selected to convert substantially all of said $C_6$–$C_{22}$ diolefins to the corresponding monoolefinic hydrocarbons and to produce a selective hydrogenation reaction zone effluent stream substantially free of $C_6$–$C_{22}$ diolefinic hydrocarbons and said liquid phase process stream is passed through a stripping zone operated at conditions to selectively separate $C_6$-minus light hydrocarbons and produce a hydrogenated effluent stream comprising $C_6$–$C_{22}$ paraffinic hydrocarbons and $C_6$–$C_{22}$ monoolefinic hydrocarbons that is passed with an aromatic hydrocarbon stream into an alkylation zone maintained at alkylation-promoting conditions to alkylate said aromatic hydrocarbon and to produce and alkylation zone effluent stream comprising alkylaromatic hydrocarbons and $C_6$–$C_{22}$ paraffinic hydrocarbons that is passed to an alkylation separation section to recover an alkylaromatic hydrocarbon stream and said recycle stream; the improvement wherein, the recycle stream is saturated, said liquid phase process stream is passed first to said stripping zone, and a liquid phase effluent from said stripping zone is passed directly to said selective hydrogenation reaction zone and the effluent from said selective hydrogenation zone is passed directly without intermediate separation from said selective hydrogenation zone into said alkylation zone, said alkylation zone contains a solid alkylation catalyst, said alkylation zone effluent contains $C_6$–$C_{22}$ monoolefinic hydrocarbons and said recycle stream is passed from said separation section through a monoolefinic hydrocarbon hydrogenation zone and contacted with a hydrogenation catalyst at hydrogenation conditions to convert essentially all of said monoolefinic hydrocarbons to paraffinic hydrocarbons and completely saturate said recycle stream.

2. The improvement of claim 1 wherein said solid alkylation catalyst is selected from the group consisting of amorphous silica-alumina, zeolite, pillared clay and acidic polymers.

3. The improvement of claim 1 wherein the selective diolefin hydrogenation catalyst comprises at least one component selected from the group consisting of palladium, nickel, and sulfur and an inorganic support material.

4. The improvement of claim 1 wherein said aromatic hydrocarbon is benzene and a $C_{10}$–$C_{22}$ paraffinic hydrocarbon is passed to said dehydrogenation reaction zone as said $C_6$–$C_{22}$ paraffinic hydrocarbon feed.

5. The improvement of claim 1 wherein said selective hydrogenation zone and said alkylation reaction zone are contained in a common reaction vessel.

6. The improvement of claim 1 wherein said $C_6$–$C_{22}$ paraffinic hydrocarbon feed is passed through said monoolefinic hydrocarbon hydrogenation zone.

7. In a process for the production of linear alkyl benzenes by the reaction of benzene with monoolefinic hydrocarbons in the presence of a solid alkylation catalyst and paraffinic hydrocarbons wherein a $C_{10}$–$C_{22}$ linear paraffinic hydrocarbon feed and a recycle stream are combined and the combined stream is passed through a dehydrogenation reaction zone maintained at dehydrogenation conditions effective to produce a vapor phase dehydrogenation reactor effluent stream comprising $C_{10}$-minus light hydrocarbons, and light hydrocarbon by-products, $C_{10}$–$C_{22}$ paraffinic hydrocarbons, $C_{10}$–$C_{22}$ linear monoolefinic hydrocarbons, $C_{10}$–$C_{22}$ diolefinic hydrocarbons and hydrogen that is cooled and partially condensed to form a vapor-liquid dehydrogenation reactor zone effluent that is passed to a vapor-liquid separation zone to separate said vapor-liquid dehydrogenation reactor effluent stream into a vapor phase process stream comprising hydrogen and a liquid phase process stream which comprises dissolved hydrogen, $C_{10}$-minus light hydrocarbons, $C_{10}$–$C_{22}$ diolefinic hydrocarbons, $C_{10}$–$C_{22}$ paraffinic hydrocarbons and $C_{10}$–$C_{22}$ linear monoolefinic hydrocarbons at least a portion of which is passed into a stripping zone operated at conditions to selectively separate and remove hydrogen and $C_{10}$-minus light hydrocarbons from said liquid phase process stream and into a selective hydrogenation reaction zone containing a selective hydrogenation catalyst and maintained at selective hydrogenation conditions, with a hydrogen feedstream in an amount selected to convert substantially of said $C_{10}$–$C_{22}$ diolefin to the corresponding monoolefinic hydrocarbon and to produce a stripped selective hydrogenation reaction zone effluent stream substantially free of $C_{10}$–$C_{22}$ diolefinic hydrocarbons and comprising hydrogen, $C_{10}$–$C_{22}$ paraffinic hydrocarbons and $C_{10}$–$C_{22}$ linear monoolefinic hydrocarbons that is passed together with a benzene feed into an alkylation zone maintained at alkylation-promoting conditions to alkylate said benzene and to produce an alkylation zone effluent stream comprising linear alkyl benzene, $C_{10}$–$C_{22}$ paraffinic hydrocarbons and $C_{10}$–$C_{22}$ monoolefinic hydrocarbons which is passed to an alkylation separation section to recover linear alkyl benzene and said recycle stream comprising $C_{10}$–$C_{22}$ paraffinic hydrocarbons; the improvement wherein, the recycle stream is saturated, said liquid phase process stream is passed first to said stripping zone, the effluent of said stripping zone is passed directly to a selective hydrogenation reaction zone, the effluent from said selective hydrogenation zone is passed directly without intermediate separation from said selective hydrogenation zone into said alkylation zone, said alkylation zone contains a solid alkylation catalyst said alkylation zone effluent contains $C_{10}$–$C_{22}$ monoolefinic hydrocarbons and said recycle stream is passed from said separation section through a monoolefinic hydrocarbon hydrogenation zone and contacted with a hydrogenation catalyst at hydrogenation conditions to convert essentially all of said monoolefinic hydrocarbons to paraffinic hydrocarbons and produce said saturated recycle stream.

* * * * *